US012683050B2

(12) United States Patent　　(10) Patent No.:　US 12,683,050 B2
Takayama et al.　　(45) Date of Patent:　Jul. 14, 2026

(54) SUPERCONDUCTING COIL APPARATUS, SUPERCONDUCTING ACCELERATOR, AND PARTICLE BEAM THERAPY APPARATUS

(71) Applicants: TOSHIBA ENERGY SYSTEMS & SOLUTIONS CORPORATION, Kawasaki (JP); National Institutes for Quantum Science and Technology, Chiba (JP)

(72) Inventors: Shigeki Takayama, Yokohama Kanagawa (JP); Tomofumi Orikasa, Yokohama Kanagawa (JP); Kota Mizushima, Narashino Chiba (JP); Yoshiyuki Iwata, Narashino Chiba (JP); Yasushi Abe, Koshigaya Saitama (JP); Tetsuya Fujimoto, Yachiyo Chiba (JP)

(73) Assignees: TOSHIBA ENERGY SYSTEMS & SOLUTIONS CORPORATION;, Kawasaki (JP); NATIONAL INSTITUTES FOR QUANTUM SCIENCE AND TECHNOLOGY, Chiba (JP)

( * ) Notice: Subject to any disclaimer, the term of this patent is extended or adjusted under 35 U.S.C. 154(b) by 565 days.

(21) Appl. No.: 18/352,740

(22) Filed: Jul. 14, 2023

(65) Prior Publication Data

US 2024/0096534 A1　　Mar. 21, 2024

Related U.S. Application Data

(63) Continuation of application No. PCT/JP2022/005377, filed on Feb. 10, 2022.

(30) Foreign Application Priority Data

Mar. 23, 2021　　(JP) ................................. 2021-048690

(51) Int. Cl.
　　*H01F 6/06*　　(2006.01)
　　*A61N 5/10*　　(2006.01)

(52) U.S. Cl.
　　CPC ............. *H01F 6/06* (2013.01); *A61N 5/1077* (2013.01); *A61N 2005/1087* (2013.01)

(58) Field of Classification Search
　　CPC . H01F 6/06; A61N 5/1077; A61N 2005/1087; A61N 5/10; H05H 7/04; H05H 13/04
　　See application file for complete search history.

(56) References Cited

U.S. PATENT DOCUMENTS

| 12,473,205 | B2 * | 11/2025 | Nakamichi | ............... C01F 3/00 |
| 2020/0365303 | A1 * | 11/2020 | Hamada | .............. H01F 27/2823 |

FOREIGN PATENT DOCUMENTS

| JP | H10-144521 A | 5/1998 |
| JP | 2009-301992 A | 12/2009 |

(Continued)

OTHER PUBLICATIONS

International Search Report with Partial English Translation of International Patent Application No. PCT/JP2022/005377 dated Apr. 19, 2022 (6 pages).

(Continued)

*Primary Examiner* — Abdullah A Riyami
*Assistant Examiner* — Syed M Kaiser
(74) *Attorney, Agent, or Firm* — Foley & Lardner LLP

(57) ABSTRACT

According to one embodiment, a superconducting coil apparatus comprising at least one superconducting coil formed of a plurality of turns under a definition that one turn is a portion of a superconducting wire annularly wound for one round, wherein: the superconducting coil has a shape along an outer peripheral surface of a tubular structure having a tubular shape; each of the plurality of turns has a coil longitudinal portion extending along an axial direction of the (Continued)

tubular structure; arrangement form of the coil longitudinal portion is different between a main magnetic field generation region configured to generate a main magnetic field and a magnetic field correction region configured to generate a correction magnetic field.

11 Claims, 11 Drawing Sheets

(56) References Cited

FOREIGN PATENT DOCUMENTS

| | | | |
|---|---|---|---|
| JP | 2010-118457 A | 5/2010 | |
| JP | 2013-206635 A | 10/2013 | |
| JP | 6758555 B1 * | 9/2020 | ............. A61B 5/055 |

OTHER PUBLICATIONS

Stephan Russenschuck, "Field Computation for Accelerator Magnets", Chapter 19, p. 612 and 633, WiLEY-VCH (3 pages).

* cited by examiner

SUPERCONDUCTING COIL APPARATUS, SUPERCONDUCTING ACCELERATOR, AND PARTICLE BEAM THERAPY APPARATUS

CROSS-REFERENCE TO RELATED APPLICATIONS

This application is a Continuation Application of No. PCT/JP2022/005377, filed on Feb. 10, 2022, and the PCT application is based upon and claims the benefit of priority from Japanese Patent Application No. 2021-048690, filed on Mar. 23, 2021, the entire contents of which are incorporated herein by reference.

TECHNICAL FIELD

Embodiments of the present invention relate to a superconducting technique.

BACKGROUND

Attention has been focused on a particle beam therapy technique in which a diseased tissue (cancer) of a patient is irradiated with a particle beam such as a carbon ion beam for treatment. This particle beam therapy technique can pinpoint and kill only the diseased tissue without damaging normal tissues. Thus, the burden on the patient is less than surgery or medication treatment, and earlier return to society after the treatment can also be expected. In order to treat cancer cells deep inside the body, it is necessary to accelerate the particle beam. In general, particle beam accelerators configured to accelerate the particle beam are broadly classified into two types. One of the two types is a linear accelerator in which accelerating apparatuses are arranged in a straight line. The other type is a circular accelerator in which deflectors configured to bend the trajectory of the particle beam are arranged circularly and an accelerator is disposed in part of this circular trajectory. In particular, in the case of using heavy particles such as carbons and protons, it is common to adopt a method in which a linear accelerator is used for acceleration in the low energy band immediately after generation of the beam and a circular accelerator is used for acceleration in the high energy band.

The circular accelerator configured to circulate and accelerate the particle beam is configured by sequentially arranging: a quadrupole electromagnet configured to control the shape of the particle beam; a bending electromagnet configured to bend the trajectory of the particle beam; a steering electromagnet configured to correct deviation of the beam trajectory; and the like. In such an accelerator, when mass or energy of the particles to be circulated increases, magnetic rigidity (i.e., difficulty of bending by the magnetic field) increases, and thus the beam trajectory radius increases. As a result, the entirety of the apparatus becomes larger in size. As the size of the apparatus increases, the incidental facilities such as the building also increase in size, and consequently, this apparatus cannot be introduced in a place where the installation range is limited, such as in an urban site. Further, in order to suppress increase in size of the apparatus, it is necessary to increase the magnetic field strength to be generated by the bending electromagnet. In a general bending electromagnet, influence of magnetic saturation of its iron core makes it difficult to generate a magnetic field exceeding 1.5 T. For this reason, it is desired to apply a superconducting technique, which can achieve both high magnetic field and miniaturization of the circular accelerator, to a bending electromagnet.

PRIOR ART DOCUMENT

Patent Document

[Patent Document 1] JP H10-144521 A
[NON-Patent Document 1] "Field Computation for Accelerator Magnets" Stephan Russenschuck WiLEY-VCH

SUMMARY

Problems to be Solved by Invention

In general, a saddle type coil is used as a conventional superconducting coil for an accelerator. In the conventional technology, spacers (gaps) are provided between the superconducting wires at the ends of the coils in order to generate a uniform magnetic field, i.e., in order to reduce high-order multipolar components. Hence, there is a problem that the coil ends are extended and the superconducting coil becomes larger in size.

Further, in the conventional technology, there is also a method of adding a correction coil in order to cancel an undesired magnetic field to be generated at the coil ends. Also in this method, it is necessary to overlap the correction coil outside the main coil, and thus, there is a problem that the size of the superconducting coil becomes larger in a radial direction, in an axial direction, or in both directions.

In view of the above-described circumstances, an object of embodiments of the present invention is to provide a superconducting technique by which size of a superconducting coil apparatus can be reduced.

DETAILED DESCRIPTION

In one embodiment of the present invention, a superconducting coil apparatus comprising at least one superconducting coil formed of a plurality of turns under a definition that one turn is a portion of a superconducting wire annularly wound for one round, wherein: the superconducting coil has a shape along an outer peripheral surface of a tubular structure having a tubular shape; each of the plurality of turns has a coil longitudinal portion extending along an axial direction of the tubular structure; arrangement form of the coil longitudinal portion is different between a main magnetic field generation region configured to generate a main magnetic field and a magnetic field correction region configured to generate a correction magnetic field.

According to embodiments of the present invention, it is possible to provide a superconducting technique by which size of a superconducting coil apparatus can be reduced.

Hereinbelow, a description will be given of embodiments of a superconducting coil apparatus, a superconducting accelerator, and a particle beam therapy apparatus in detail by referring to the accompanying drawings.

Figure 1:
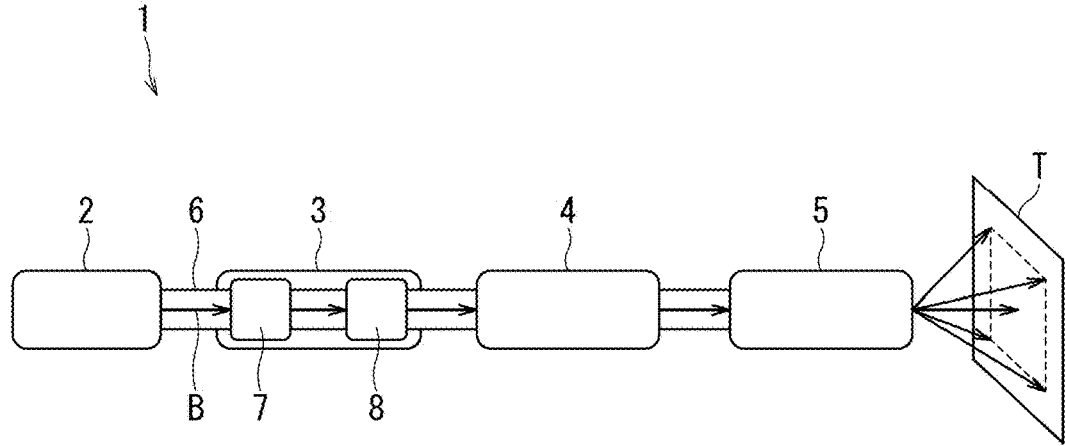
FIG. 1 is a conceptual diagram illustrating a particle beam therapy apparatus according to the present embodiment.

The reference sign 1 in FIG. 1 denotes a particle beam therapy apparatus according to the present embodiment. The particle beam therapy apparatus 1 is a beam irradiation apparatus that accelerates a particle beam B and irradiates a lesion site T, i.e., the target with this particle beam B for treatment.

The particle beam therapy apparatus 1 uses charged particles (for example, negative pions, protons, helium ions, carbon ions, neon ions, silicon ions, and argon ions) as the particle beam B for therapeutic irradiation.

The particle beam therapy apparatus 1 includes: a beam generator 2; a beam accelerator 3; a beam transport apparatus 4; a beam irradiator 5; and vacuum duct 6, by which these components are connected and through which the particle beam B passes.

The vacuum duct 6 maintains their inside in a vacuum state. The particle beam B passes through the inside of the vacuum duct 6, and thereby, beam-loss due to scattering between the particle beam B and air is suppressed. The vacuum duct 6 extends to just before the position of the lesion site T of the patient. The particle beam B having passed through the vacuum duct 6 is radiated onto the lesion site T of the patient.

The beam generator 2 is an apparatus that generates the particle beam B and is, for example, an apparatus that extracts ions generated by using an electromagnetic field, a laser, or the like.

The beam accelerator 3 is disposed on the downstream side of the beam generator 2. The beam accelerator 3 is an apparatus that accelerates the particle beam B to a predetermined energy. The beam accelerator 3 is composed of a front-stage accelerator and a rear-stage accelerator, for example. As the front-stage accelerator, a linear accelerator 7 configured of a drift tube linac (DTL) or a radio-frequency quadrupole linear accelerator (RFQ) is used. As the rear-stage accelerator, a circular accelerator 8 configured of a synchrotron or a cyclotron is used. The beam trajectory of the particle beam B is famed by the linear accelerator 7 and the circular accelerator 8.

The beam transport apparatus 4 is disposed on the downstream side of the beam accelerator 3. The beam transport apparatus 4 is an apparatus configured to transport the accelerated particle beam B to the patient's lesion site T as the irradiation target. The beam transport apparatus 4 is composed of deflectors, focusing/defocusing apparatuses, a hexapole apparatus, a beam trajectory correction apparatus, its controller, and the like which are arranged around the vacuum duct 6.

The beam irradiator 5 is disposed at the downstream of the beam transport apparatus 4. The beam irradiator 5 controls the beam trajectory of the particle beam B and monitors the irradiation position and irradiation dose of the particle beam B at the lesion site T so as to accurately irradiate the irradiation point having been set at the lesion site T of the patient with the particle beam B, which has passed through the beam transport apparatus 4 and has a predetermined energy.

In the beam accelerator 3 and the beam transport apparatus 4, a superconducting technique which can achieve both the high magnetic field and miniaturization is used. In the present embodiment, the circular accelerator 8 of the beam accelerator 3 is illustrated as an application aspect of the superconducting technique. In other words, the particle beam therapy apparatus 1 according to the present embodiment includes the circular accelerator 8 as a superconducting accelerator. At least part of the beam trajectory for accelerating the particle beam B is formed by the circular accelerator 8.

Figure 2:
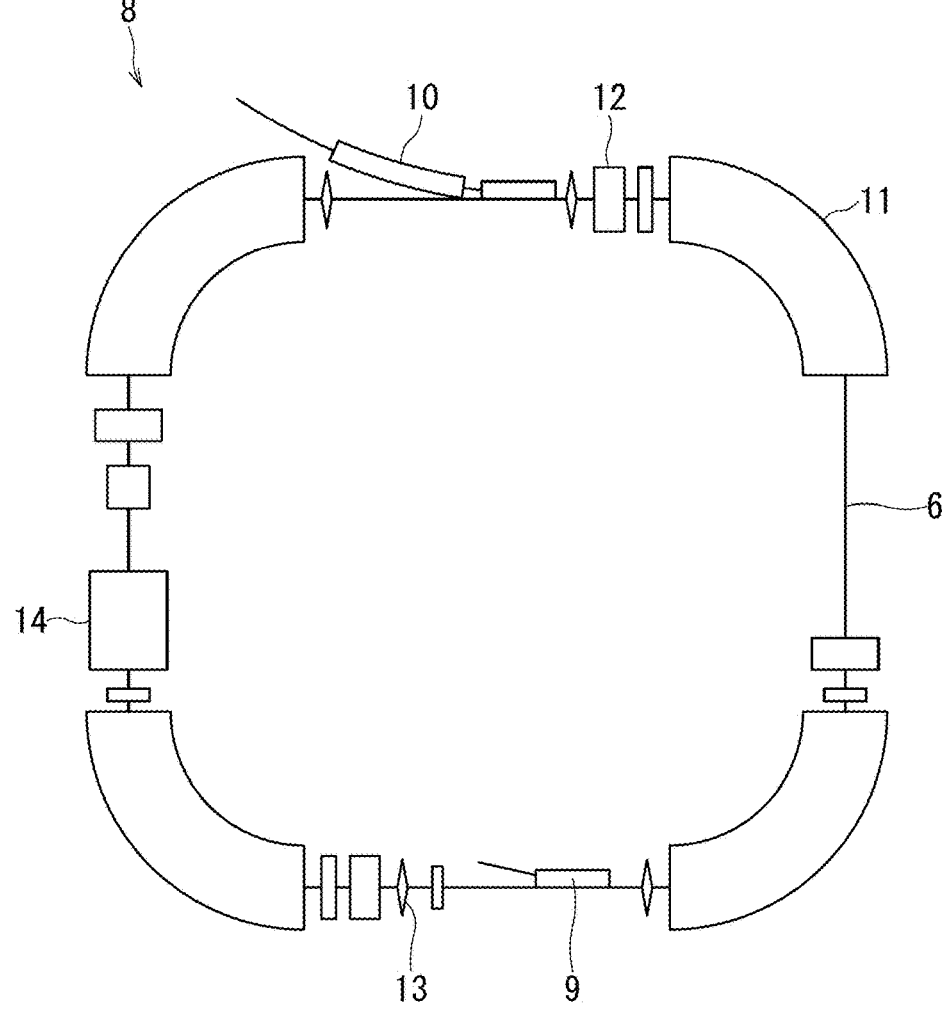
FIG. 2 is a plan view of a circular accelerator.

As shown in FIG. 2, the circular accelerator 8 as the superconducting accelerator of the present embodiment is built along the vacuum duct 6, which are formed annularly (i.e., approximately in a circular shape) in plan view. The circular accelerator 8 includes: a beam injector 9; a beam emitter 10; deflectors 11; focusing/defocusing apparatuses 12; hexapole apparatuses 13; and an acceleration-force application apparatus 14.

The circular accelerator 8 circulates the particle beam B along the vacuum duct 6 by deflecting the trajectory of the particle beam B injected from the linear accelerator 7 via the beam injector 9 with the use of the deflectors 11. The particle beam B is stably circulated by using the focusing/defocusing apparatuses 12 and the hexapole apparatuses 13.

When the particle beam B circulates the beam trajectory of the circular accelerator 8, acceleration force is applied to the particle beam B by the acceleration-force application apparatus 14. Further, the particle beam B is accelerated to a predetermined energy, and this accelerated particle beam B is emitted from the beam emitter 10 so as to reach the lesion site T.

Although the deflectors 11 deflect the particle beam B by the magnetic field in the circular accelerator 8, when the mass or energy of the particles to be circulated is increased, the magnetic rigidity (i.e., difficulty in bending by the magnetic field) is increased, and thereby the beam trajectory radius becomes larger. As a result, the circular accelerator 8 becomes larger in size as a whole. In order to suppress the increase in size of the circular accelerator 8, it is necessary to increase the magnetic field strength to be generated by the deflectors 11. In the present embodiment, magnetic field strength can be enhanced and the size of the circular accelerator 8 can be reduced by applying a superconducting technology to the deflectors 11.

Here, superconducting wires are composed of: low-temperature superconductors such as NbTi, $Nb_3Sn$, $Nb_3Al$, and $MgB_2$; and high-temperature superconductors such as a $Bi_2Sr_2Ca_2Cu_3O_{10}$ wire and a $REB_2C_3O_7$ wire.

In the above notation, "RE" in "REB$_2$C$_3$O$_7$" means at least one of rare earth elements (for example, neodymium (Nd), gadolinium (Gd), holmium (Ho), and samarium (Sm)) and yttrium elements. Additionally, "B" means barium (Ba), "C" means copper (Cu), and "O" means oxygen (O).

In the case of using the low-temperature superconductors, a curved surface can be readily formed because the low-temperature superconductors have ductility. In the case of using the high-temperature superconductors, the superconducting state occurs at high temperatures, which reduces the cooling load and improves the operating efficiency.

Figure 14:
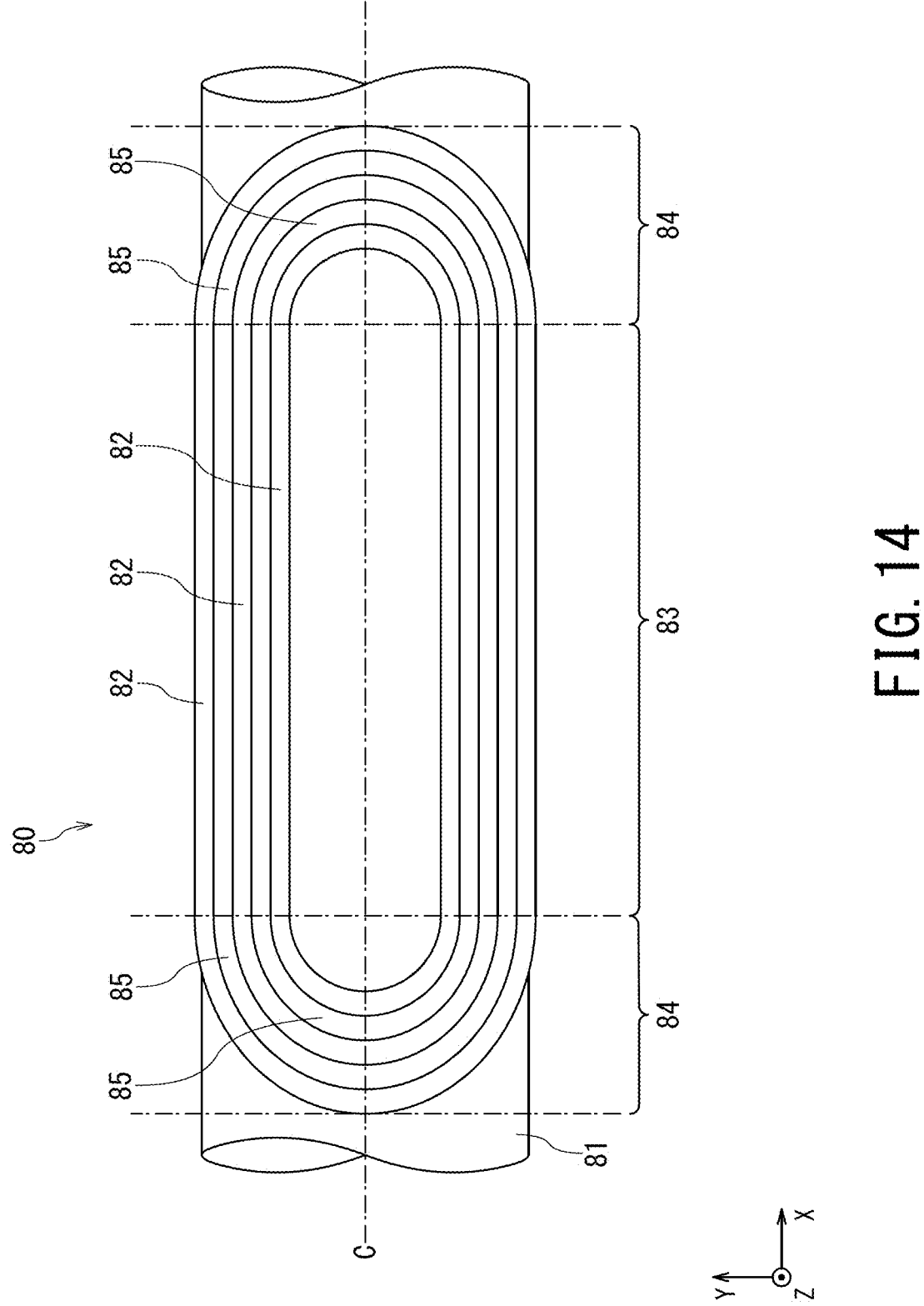
FIG. 14 is a plan view of a conventional superconducting coil.

Next, a conventional general superconducting coil 80 will be described by referring to FIG. 14. The superconducting coil 80 is provided on a side surface of a cylindrical tubular structure 81. This superconducting coil 80 includes a plurality of conductor portions 82 around which superconducting wires are wound. Each conductor portion 82 is divided into a coil longitudinal portion 83 and coil end portions 84. In the coil longitudinal portion 83, the spacings in the circumferential direction between the conductor portions 82 are not uniform, and desired magnetic field distribution is generated in the beam passage region at the central portion of the superconducting coil 80 depending on the distance.

Here, current density distribution corresponding to a magnetic field to be generated by the general superconducting coil 80 will be described. In a cross-sectional view of the tubular structure 81, a predetermined position in the circumferential direction of the tubular structure 81 is represented by an angle $\theta$ of the central axis.

For example, in the case of generating a dipole magnetic field that is a uniform magnetic field, the conductor portions 82 in the coil longitudinal portion 83 are arranged in such a manner that the current density distribution is close to a function of $\cos \theta$. Similarly, in the case of generating a quadrupole magnetic field, the conductor portions 82 in the coil longitudinal portion 83 are arranged in such a manner that the current density distribution is close to a function of $\cos 2\theta$. In the case of generating a hexapole magnetic field, the conductor portions 82 in the coil longitudinal portion 83 are arranged in such a manner that the current density distribution is close to a function of $\cos 3\theta$. In the case of generating an octupole magnetic field, the conductor portions 82 in the coil longitudinal portion 83 are arranged in such a manner that the current density distribution is close to a function of $\cos 4\theta$.

Each coil end portion 84 has a three-dimensional shape along the surface of the tubular structure 81 so that the conductor portions 82 forming the coil end portions 84 do not physically block the beam passage region. Thus, each coil end portion 84 has a shape in which the conductor gradually transitions from the side surface to the top surface of the tubular structure 81.

In each coil end portion 84, current density distribution different from the current density distribution to be generated in the coil longitudinal portion 83 is generated. Thus, an error magnetic field (unnecessary magnetic field component) being disturbed from the desired magnetic field distribution is generated. For example, in the case of generating a dipole magnetic field, at each coil end portion 84, the conductor portion 82 changes from the position of $\theta=0°$ to the position of $\theta=90°$. At this time, the current density distribution such as $\cos 2\theta$ or $\cos 3\theta$ is superimposed on the current density distribution of $\cos \theta$. Thus, a negative hexapole magnetic field (hexapole component) is generated.

In the conventional technology, spacers 85 (gaps) are provided for the coil end portions 84 in order to suppress this negative hexapole magnetic field. Further, a positive hexapole magnetic field is generated by maintaining the conductor portions 82 provided near the position of $\theta=0°$, and thereby a desired uniform magnetic field is obtained. However, in this method, the coil end portions 84 are extended, thereby the overall dimension of the superconducting coil 80 is increased, and consequently, the overall size of the circular accelerator 8 is increased. For this reason, in the present embodiment, a desired uniform magnetic field is obtained and the size of the superconducting coil 80 is reduced by appropriately arranging the superconducting wires.

Next, a description will be given of the superconducting coil apparatus 20 provided in the circular accelerator 8 as the superconducting accelerator of the present embodiment by using FIG. 3 to FIG. 12. In the following description regarding the superconducting coil apparatus 20, when an axial direction in which the particle beam B passes (i.e., the direction in which the axis C extends) is defined an X-axis direction, the state of the superconducting coil apparatus 20 as viewed from a Y-axis direction is defined as a side view, and the state of the superconducting coil apparatus 20 as viewed from a Z-axis direction is defined as a plan view (top view). Although the superconducting coil apparatus 20 is not an apparatus to be affected by gravity and there is no distinction between which side is up and down, it is assumed for convenience that the Z-axis direction is the upward direction of the superconducting coil apparatus 20.

Figure 9:
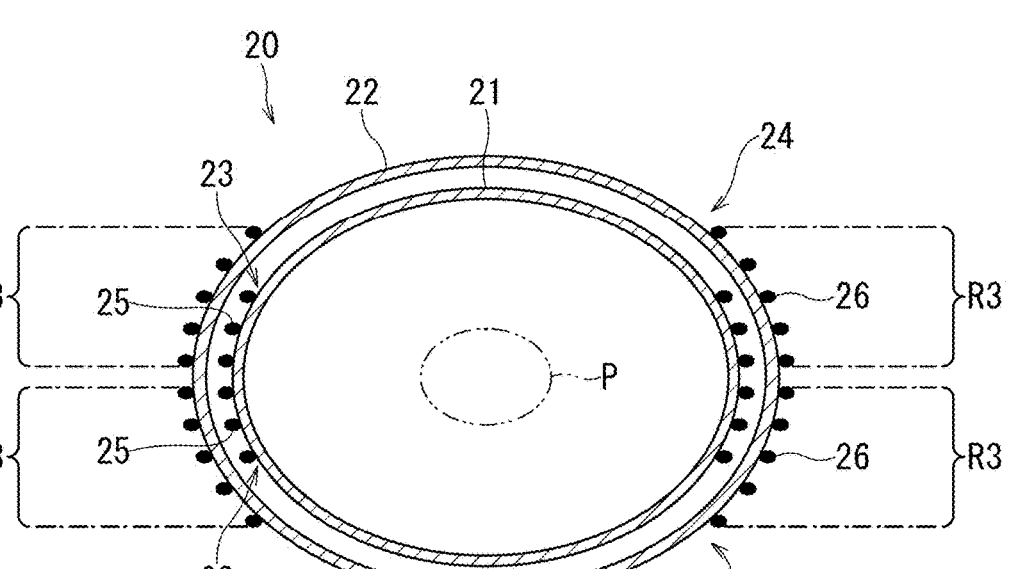
FIG. 9 is a cross-sectional view taken along the line IX-IX of FIG. 8.

First, as shown in FIG. 9, the superconducting coil apparatus 20 of the present embodiment has a two-layer structure. This superconducting coil apparatus 20 includes: a first-layer tubular structure 21 that is disposed on the innermost circumference and forms a tubular shape; and a second-layer tubular structure 22 that is disposed on the outer circumference of the first-layer tubular structure 21 and forms a tubular shape. These tubular structures 21 and 22 are arranged concentrically around the axis C, in other words, arranged coaxially with each other.

As shown in FIG. 3 to FIG. 6, the superconducting coil apparatus 20 includes two superconducting coils 23 provided above and below the tubular structure 21 of the first layer. As shown in FIG. 7 to FIG. 10, the superconducting coil apparatus 20 includes two superconducting coils 24 provided above and below the tubular structure 22 of the second layer. In other words, at least two superconducting coils 23 and 24 are laminated in a radial direction of the tubular structures 21 and 22. These superconducting coils 23 and 24 can generate a magnetic field in the passage region P of the particle beam B.

Figure 4:
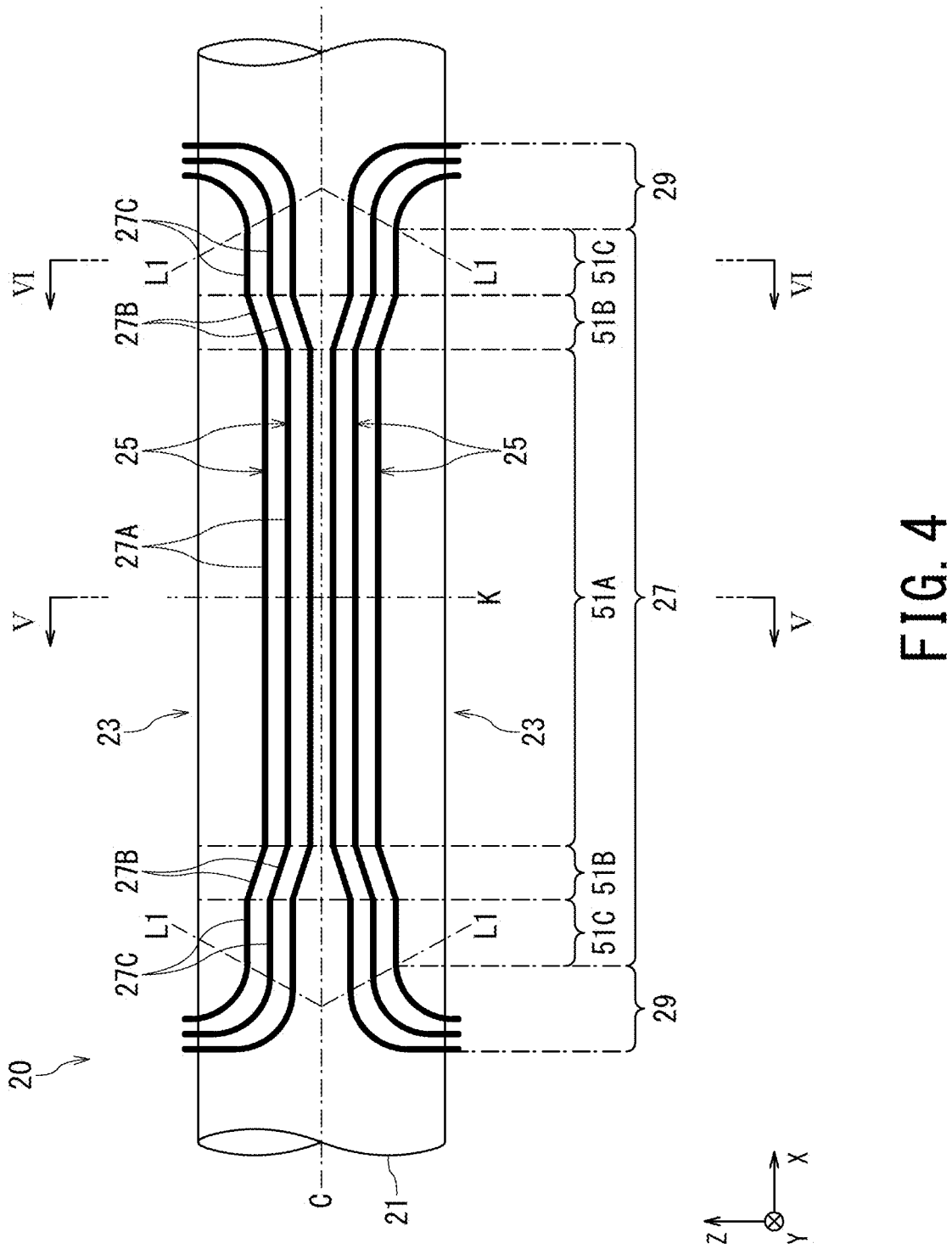
FIG. 4 is a side view of the superconducting coil of the first layer.
Figure 8:
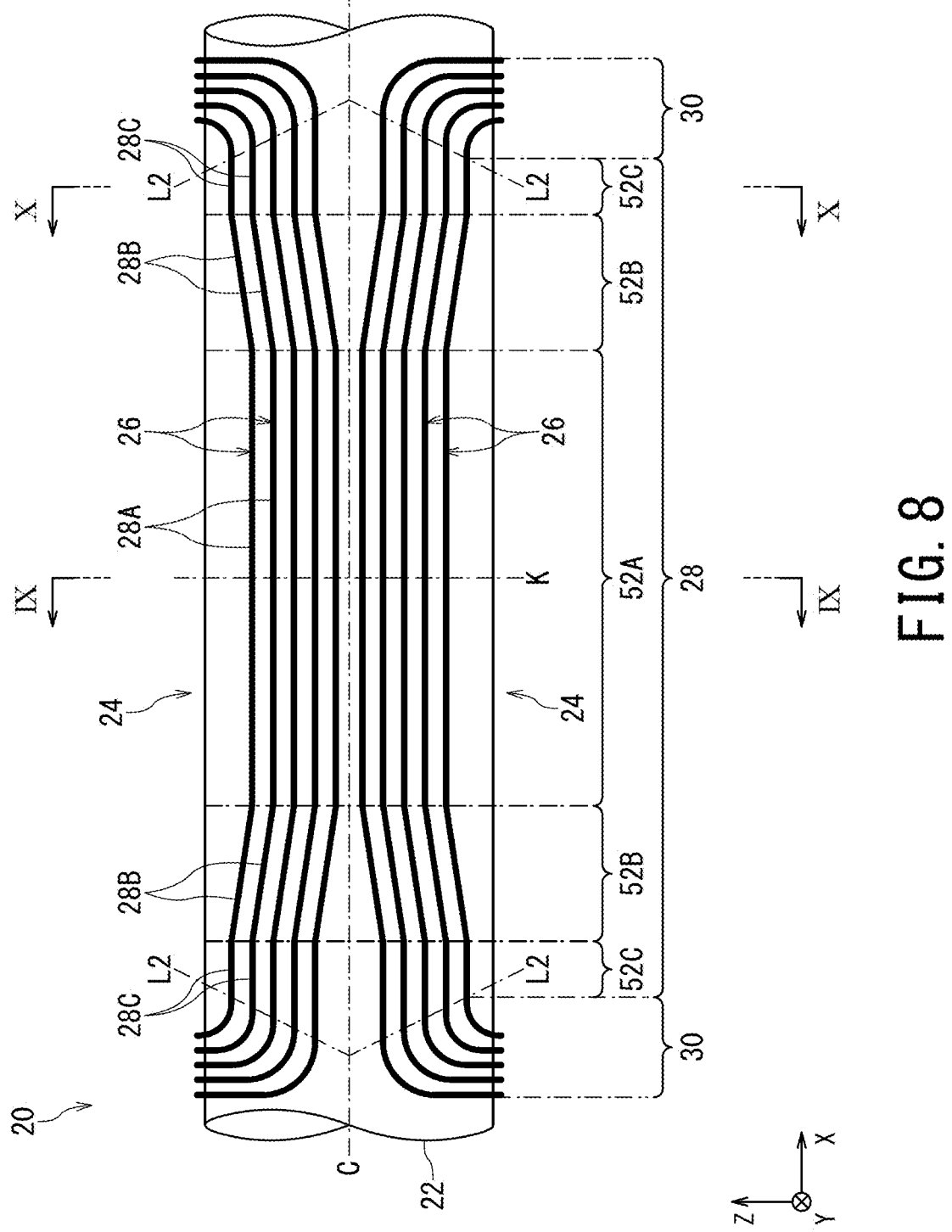
FIG. 8 is a side view of the superconducting coil of the second layer.

As shown in FIG. 9, layers of the two superconducting coils 23 and 24 are provided in the upper halves of the tubular structures 21 and 22 of the respective layers, and layers of the superconducting coils 23 and 24 are provided in the lower halves of the tubular structures 21 and 22 of the respective layers (FIG. 4 and FIG. 8).

Each of the superconducting coils 23 and 24 has a shape along the outer peripheral surface of the tubular structure 21 or 22. The tubular structures 21 and 22 are members that support the superconducting coils 23 and 24. The tubular structure 21 of the innermost first layer is disposed at the axis C of the superconducting coil apparatus 20. This first-layer tubular structure 21 forms part of the vacuum duct 6. This tubular structure 21 may be a separate member from the vacuum duct 6. In other words, the vacuum duct 6 may be provided inside the tubular structure 21.

Figure 3:
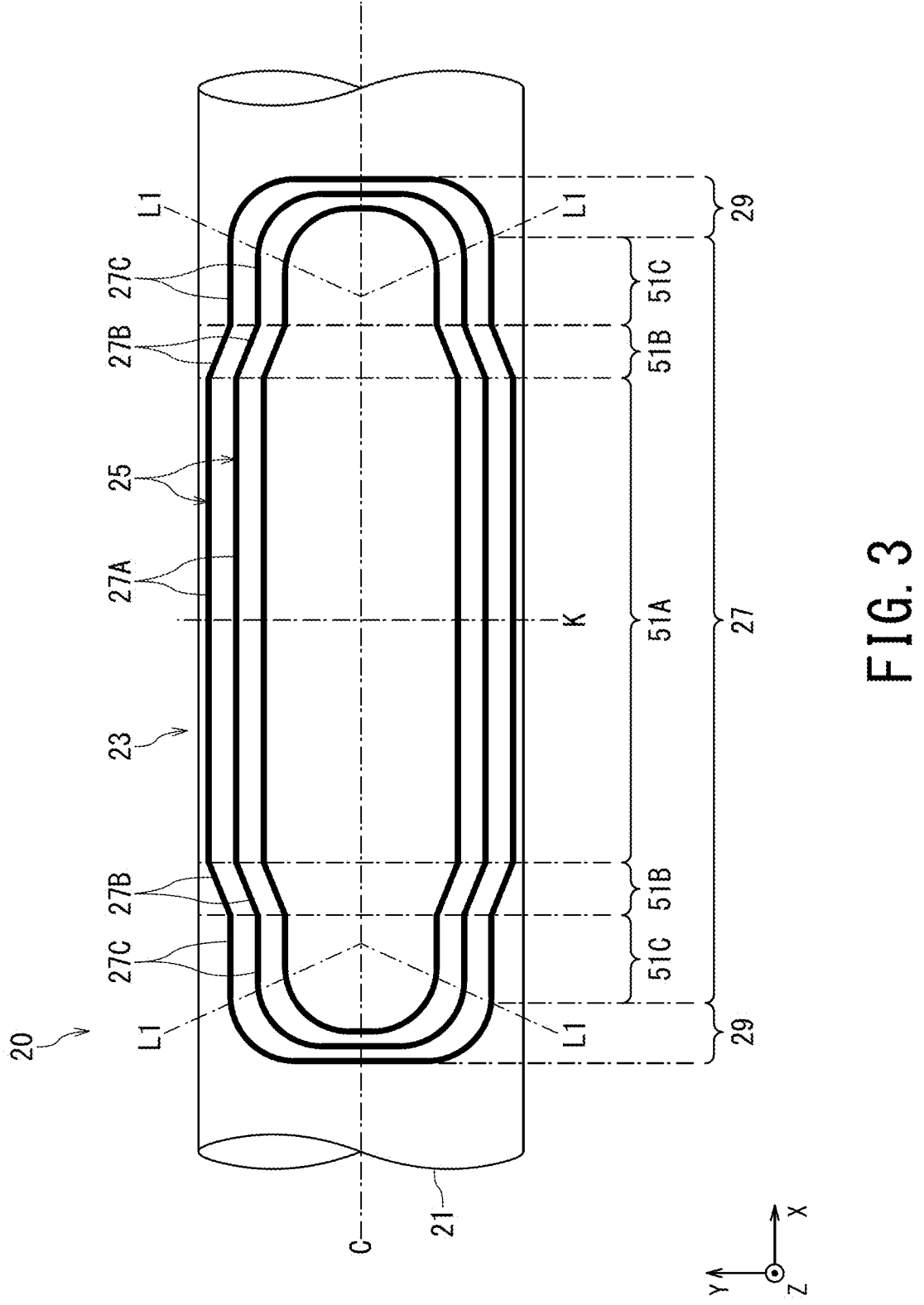
FIG. 3 is a plan view of a superconducting coil of a first layer.
Figure 7:
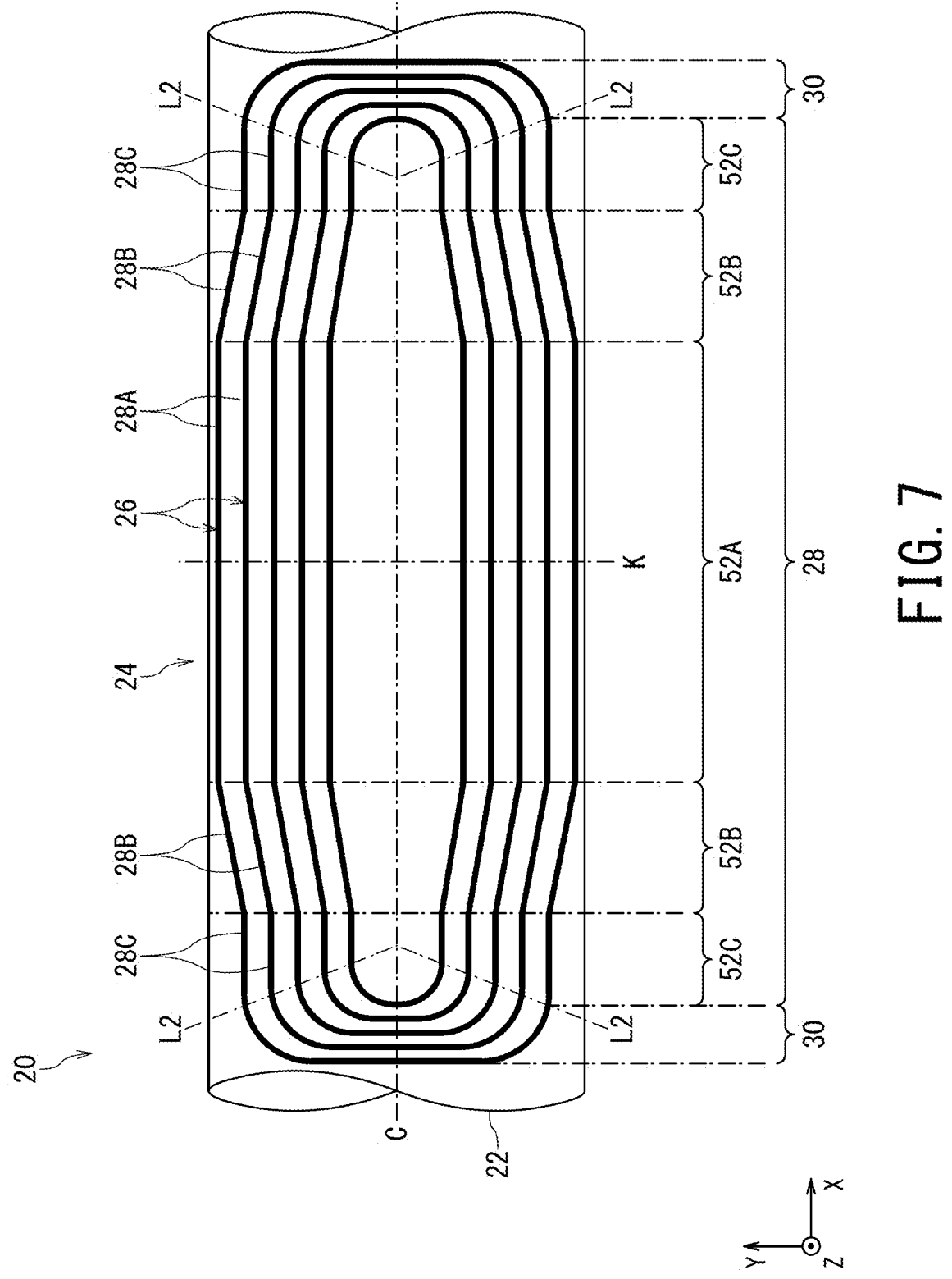
FIG. 7 is a plan view of a superconducting coil of a second layer.

The superconducting coils 23 and 24 are foiled by winding superconducting wires into an annular shape. For example, when one turn 25 (or 26) is defined as the portion of the superconducting wire wound for one round, one superconducting coil 23 (or 24) is formed by a plurality of turns 25 (or 26). In order to facilitate understanding, FIG. 3 shows a case where three turns 25 form one superconducting coil 23. FIG. 7 shows a case where five turns 26 form one superconducting coil 24. Actually, one superconducting coil 23 or 24 is formed by tens to hundreds of turns 25 or 26.

Since the tubular structure 22 of the second layer has a wider outer peripheral surface than the tubular structure 21 of the first layer, more turns 26 can be arranged in the superconducting coil 24 of the second layer than in the superconducting coil 23 of the first layer.

The superconducting coil apparatus 20 is applied to, for example, the deflectors 11 of the circular accelerator 8 (FIG. 2). The deflectors 11 are provided with the vacuum duct 6 curved with a constant curvature. Thus, the tubular structures 21 and 22 to be used in the actual superconducting coil apparatus 20 are also members curved with a constant curvature. However, in order to facilitate understanding, in FIG. 3, FIG. 4, FIG. 7, FIG. 8, FIG. 11, and FIG. 12, the tubular structures 21 and 22 are shown as straight members. Similarly, the axis C of each of the tubular structures 21 and 22 is actually curved with a constant curvature but is shown as a straight line.

As shown in FIG. 5, FIG. 6, FIG. 9, and FIG. 10, the tubular structures 21 and 22 are elliptic in cross-section. For example, when the tubular structures 21 and 22 are curved in the Y-axis direction, each of the tubular structures 21 and 22 has an elliptic shape in which the diameter in the Y-axis direction is larger than the diameter in the Z-axis direction. In other words, the tubular structures 21 and 22 are elliptic in shape with increasing diameter in the curving direction. In this manner, the superconducting coil apparatus 20 can generate a magnetic field suitable for the bending direction of the particle beam B.

As shown in FIG. 4 and FIG. 8, in the superconducting coils 23 and 24, each turn 25 (or 26) includes: a coil longitudinal portion 27 (or 28) extending linearly along the axial direction (i.e., the X-axis direction) of the tubular structure 21 (or 22); and coil end portions 29 (or 30) extending from the coil longitudinal portion 27 (or 28) along the circumferential direction of the tubular structures 21 (or 22).

In the present embodiment, in a side view of the tubular structure 21 (or 22), boundary lines L1 (or L2) for demarcating the border between the coil longitudinal portion 27 (or 28) and the coil end portions 29 (or 30) at the respective turns 25 (or 26) are inclined with respect to a reference line K extending in the circumferential direction of the tubular structure 21 (or 22). For example, the boundary line L1 of the superconducting coil 23 of the first layer and the boundary line L2 of the superconducting coil 24 of the second layer are inclined in the same direction with respect to the reference line K.

As shown in FIG. 3 and FIG. 7, in the turns 25 and 26 of the superconducting coils 23 and 24, the coil longitudinal portions 27 and 28 become shorter from the outer peripheral side to the inner peripheral side of the superconducting coils 23 and 24. Thus, the boundary lines L1 and L2 are inclined with respect to the reference line K. In this manner, the coil longitudinal portions 27 and 28 of the superconducting coils 23 and 24 of the respective layers can change the forms of the magnetic fields to be generated at their ends.

As shown in FIG. 3 and FIG. 7, in the present embodiment, the region in which the coil longitudinal portion 27 (or 28) is provided is divided into: a main magnetic field generation region 51A (or 52A); transition regions 51B (or 52B); and magnetic field correction regions 51C (or 52C).

The main magnetic field generation regions 51A and 52A are regions where the main magnetic fields are generated by the superconducting coils 23 and 24. The main magnetic field generation region 51A (or 52A) is the central portion of the coil longitudinal portion 27 (or 28) in the axial direction (i.e., the X-axis direction) of the tubular structure 21 (or 22).

The magnetic field correction regions 51C and 52C are regions for generating correction magnetic fields near the ends of the superconducting coils 23 and 24. Each magnetic field correction region 51C (or 52C) is provided at the end of the coil longitudinal portion 27 (or 28) in the axial direction (i.e., the X-axis direction) of the tubular structure 21 (or 22). The magnetic fields to be generated by the ends of the coil longitudinal portions 27 and 28 can be corrected by the magnetic field correction regions 51C and 52C.

Each transition region 51B (or 52B) is the region provided between the main magnetic field generation region 51A (or 52A) and the magnetic field correction region 51C (or 52C). Each transition region 51B (or 52B) allows the magnetic field to smoothly and continuously transition from the end of the main magnetic field generation region 51A (or 52A) to the magnetic field correction region 51C (or 52C).

Each coil longitudinal portion 27 (or 28) includes: a base part 27A (or 28A); a tapered part 27B (or 28B); and an offset part 27C (or 28C). The base parts 27A and 28A are portions corresponding to the main magnetic field generation regions 51A and 52A. The tapered parts 27B and 28B are portions corresponding to the transition regions 51B and 52B. The offset parts 27C and 28C are portions corresponding to the magnetic field correction regions 51C and 52C.

In the present embodiment, the arrangement form of the turns 25 (or 26) of the coil longitudinal portion 27 (or 28) is different between: the main magnetic field generation region 51A (or 52A); the transition regions 51B (or 52B); and the magnetic field correction regions 51C (or 52C).

For example, as shown in FIG. 4 and FIG. 8, in a side view of the tubular structures 21 and 22, the offset parts 27C (or 28C) of the coil longitudinal portion 27 (or 28) are displaced in the circumferential direction of the tubular structure 21 (or 22). As shown in FIG. 3 and FIG. 7, in a side view of the tubular structures 21 and 22, the offset parts 27C and 28C are displaced toward the inner peripheral side of the superconducting coils 23 and 24. In this manner, the magnetic fields to be generated by the magnetic field correction regions 51C and 52C can be made different (in form) from the magnetic fields to be generated by the main magnetic field generation regions 51A and 52A.

Figure 5:
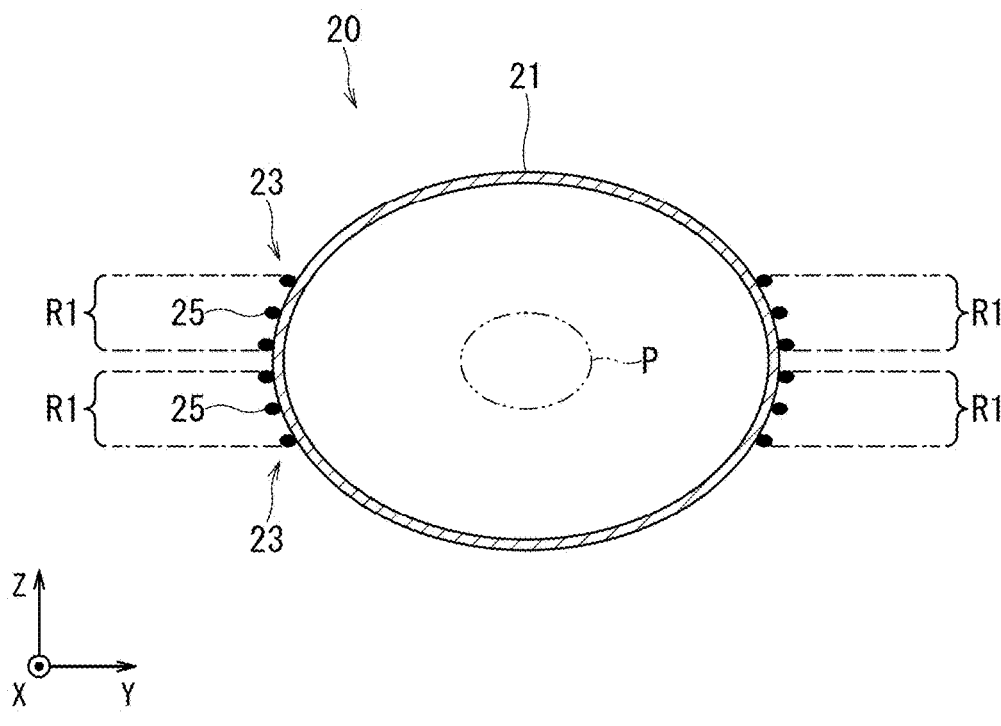
FIG. 5 is a cross-sectional view taken along the line V-V of FIG. 4.
Figure 6:
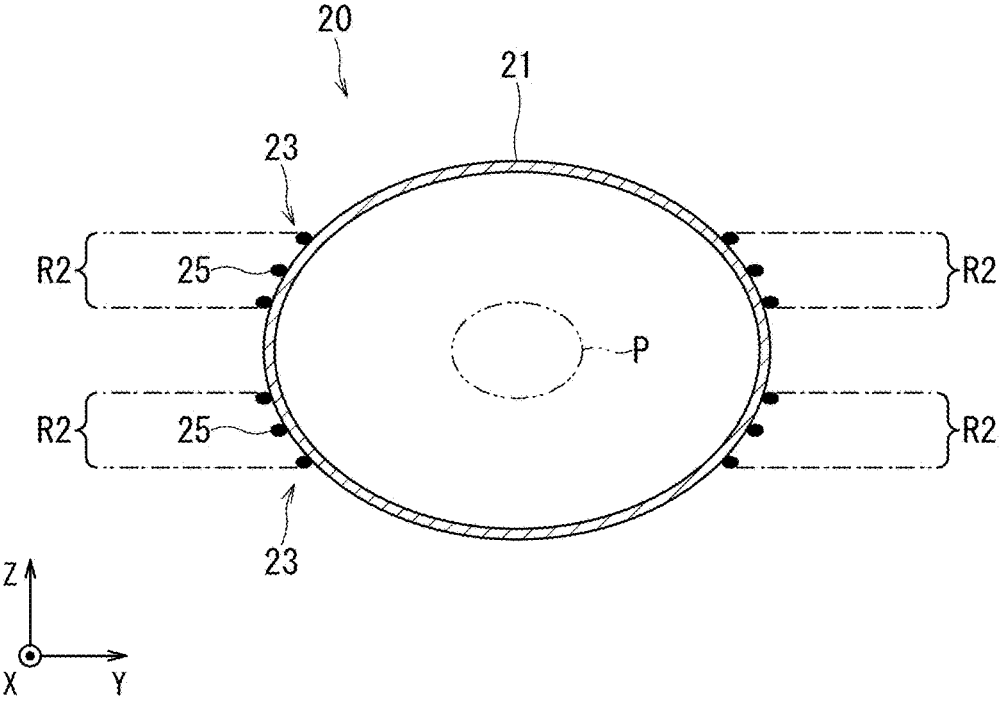
FIG. 6 is a cross-sectional view taken along the line VI-VI of FIG. 4.

As shown in FIG. 5 and FIG. 6, in a side view of the tubular structure 21, the range R1 in which the base part 27A of the first layer is provided is different from the range R2 in which the offset parts 27C are provided. The offset parts 27C are disposed above or below the base part 27A so as to be shifted (be offset).

Figure 10:
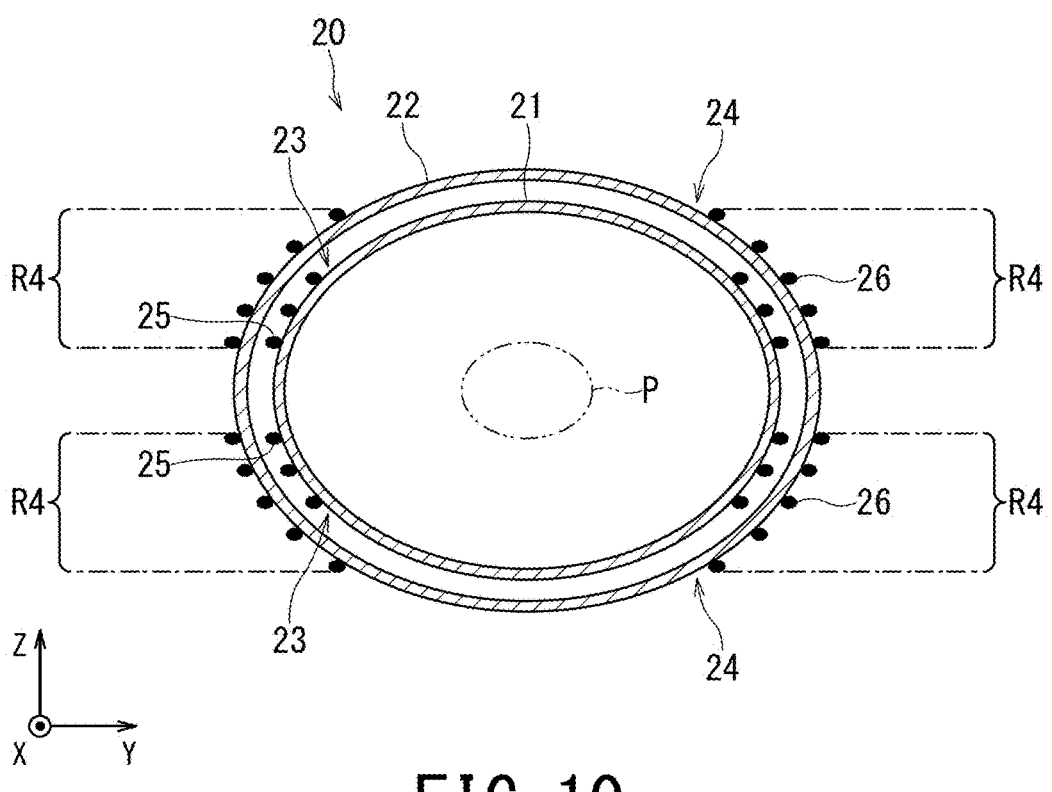
FIG. 10 is a cross-sectional view taken along the line X-X of FIG. 8.

As shown in FIG. 9 and FIG. 10, in a side view of the tubular structure 22, the range R3 in which the base part 28A of the second layer is provided is different from the range R4 in which the offset parts 28C are provided. The offset parts 28C are disposed above or below the base part 28A so as to be shifted (be offset).

In addition, the range R1 in which the base part 27A of the first layer is provided is different from the range R3 in which the base part 28A of the second layer is provided. Further, the range R2 in which the offset parts 27C of the first layer are provided is different from the range R4 in which the offset parts 28C of the second layer are provided.

The magnetic field correction regions 51C and 52C generate the magnetic fields that cancel at least the strong error magnetic fields to be generated at the coil ends 29 and 30. In this manner, when the width (i.e., length in the X-axis direction) of the coil ends 29 and 30 is reduced, the error magnetic fields to be generated at the coil ends 29 and 30 can be canceled. As described above, the superconducting coils 23 and 24 with smaller error magnetic fields can be achieved by shortening the coil ends 29 and 30.

The magnetic fields to be generated by the magnetic field correction regions 51C and 52C may be generated as predetermined magnetic fields based on the magnetic field distribution required for the superconducting coils 23 and 24, in addition to the function of canceling the error magnetic fields. For example, the magnetic fields to be generated by the magnetic field correction regions 51C and 52C may reinforce the main magnetic fields to be generated by the main magnetic field generation regions 51A and 52A or may be used for superimposing the optimum high-order multipole components in terms of beam optics. In addition, the high-order multipole components to be superimposed may be an arbitrary position other than the coil ends, and different high-order multipole components may be added on the upstream side and the downstream side of the coils.

In addition, as shown in FIG. 4 and FIG. 8, in a side view of the tubular structures 21 and 22, each tapered part 27B (or 28B) of each coil longitudinal portion 27 (or 28) is inclined with respect to the base part 27A (or 28A) and the offset part 27C (or 28C). In this manner, smoothly continuous magnetic fields can be formed from the main magnetic field generation region 51A (or 52A) to the magnetic field correction regions 51C (or 52C).

Figure 11:
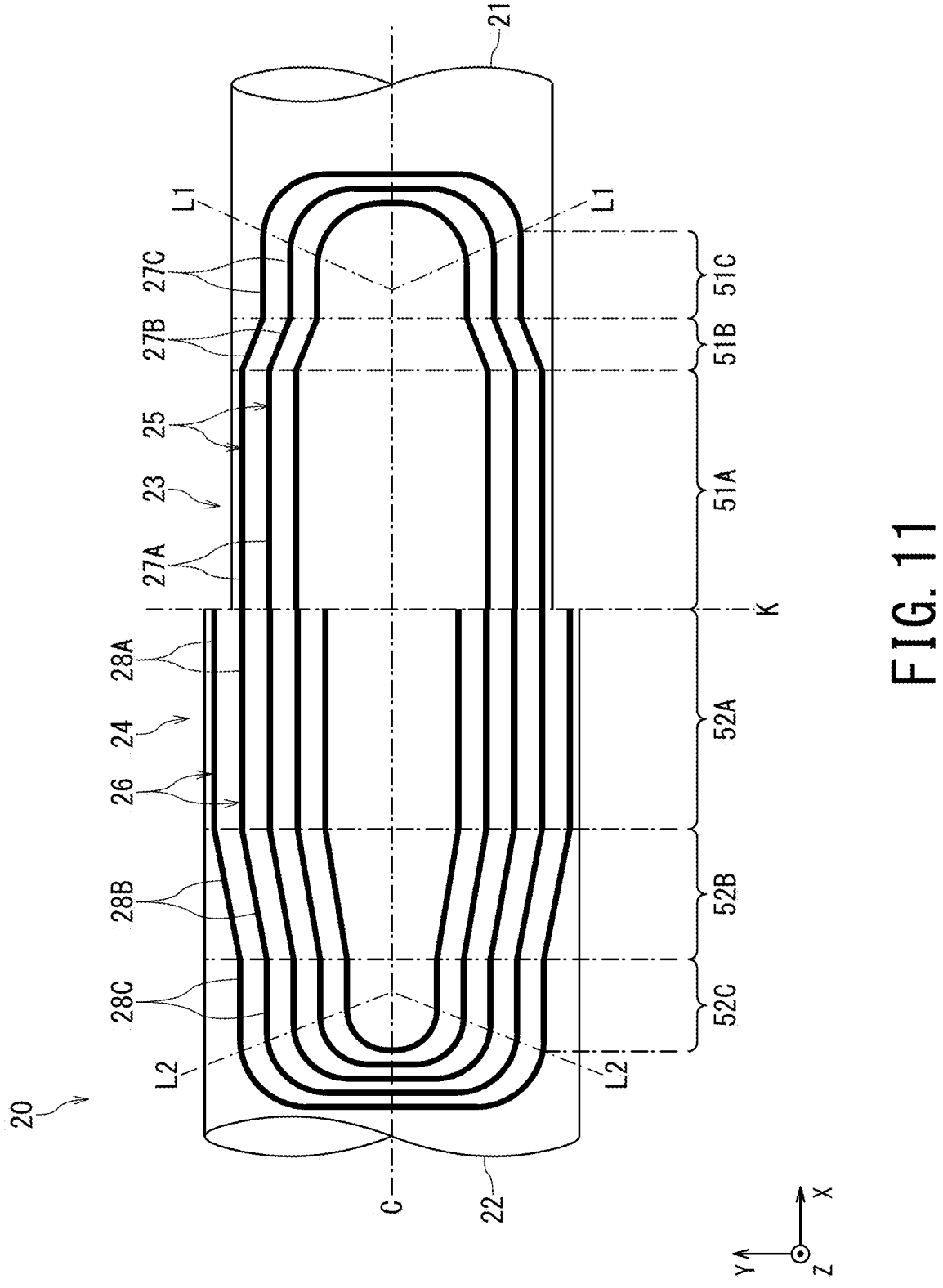
FIG. 11 is a plan view illustrating a state in which the superconducting coils of the first layer and the second layer are overlaid.
Figure 12:
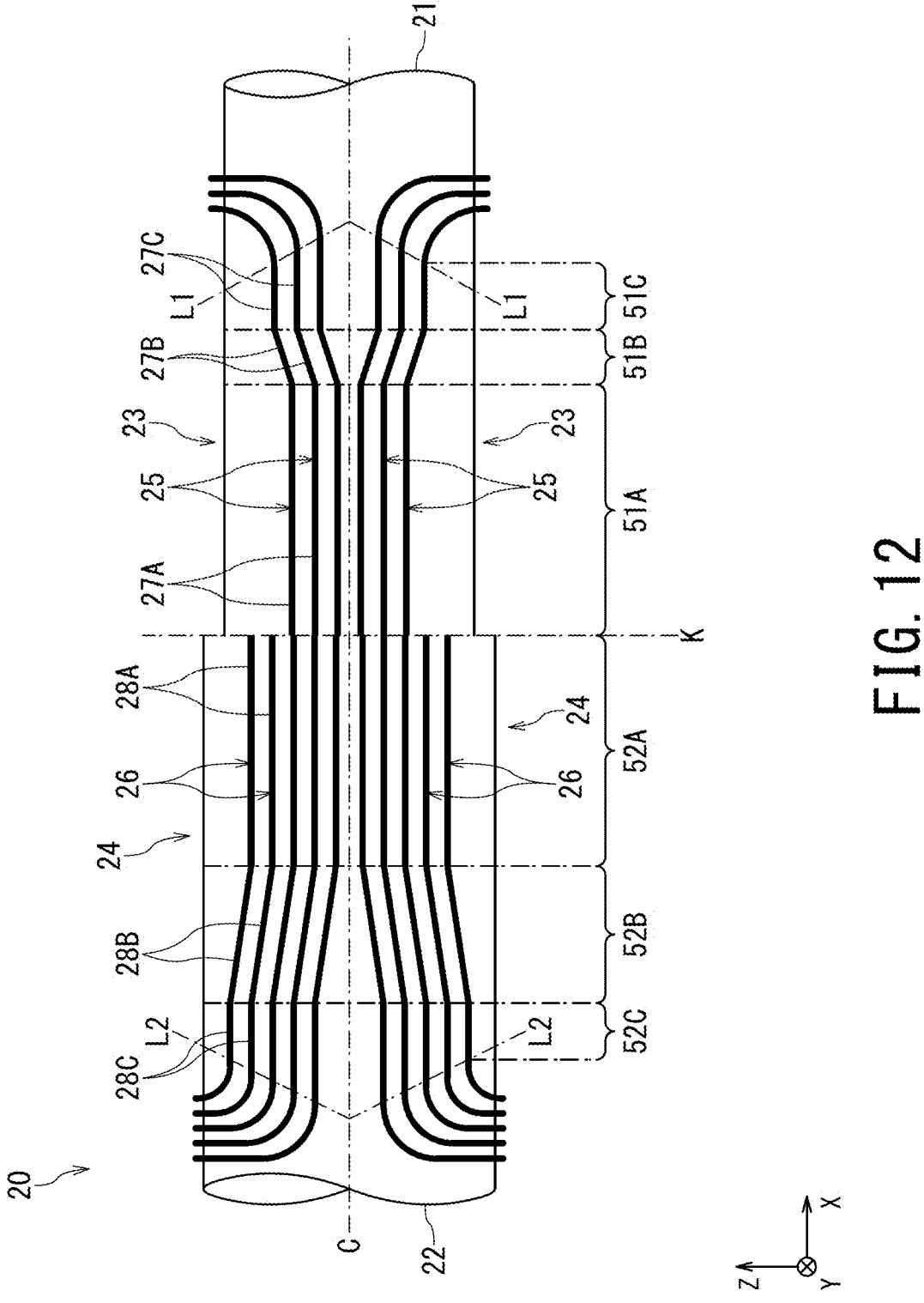
FIG. 12 is a side view illustrating a state in which the superconducting coils of the first layer and the second layer are overlaid.

As shown in FIG. 11 and FIG. 12, the axial dimension (i.e., dimension in the X-axis direction) of the transition region 51B of the superconducting coil 23 of the first layer is different from the axial dimension of the transition region 52B of the superconducting coil 24 of the second layer. For example, the axial dimension of the transition region 52B of the second layer is larger than the axial dimension of the transition region 51B of the first layer. In this manner, an appropriate magnetic field can be formed by the superconducting coil 23 of the first layer and the superconducting coil 24 of the second layer. The axial dimension (i.e., dimension in the X-axis direction) of each magnetic field correction region 51C of the first layer is different from the axial dimension of each magnetic field correction region 52C of the second layer.

The superconducting coil apparatus 20 of the present embodiment can suppress occurrence of error magnetic fields (unnecessary magnetic field components) being disturbed from the desired magnetic field distribution near the ends of the superconducting coils 23 and 24. For example, the error magnetic fields at the ends of the superconducting coil 23 of the first layer can be canceled by the magnetic fields to be generated at the ends of the superconducting coil 24 of the second layer.

In the present embodiment, the respective turns 25 and 26 (i.e., superconducting wires) can be densely arranged at the coil ends 29 and 30. Thus, the width (i.e., length in the X-axis direction) of the coil ends 29 and 30 can be reduced.

Since the plurality of superconducting coils 23 and 24 are laminated in the radial direction of the tubular structures 21 and 22, many turns 25 and 26 (i.e., superconducting wires) can be arranged in the circumferential direction in a cross-sectional view of the tubular structures 21 and 22. Thus, a stronger magnetic field can be generated. As the tubular structures 21 and 22 are laminated in the radial direction, the outer circumference length is enlarged, so more turns 26 can be arranged in the outer layer (i.e., the second layer) than in the inner layer (i.e., the first layer). A stronger magnetic field can be generated by arranging many turns 25 and 26 with smaller number of layers.

When the number of the turns 25 and 26 (i.e., superconducting wires) changes in each layer, the width (i.e., length in the X-axis direction) of the coil ends 29 and 30 changes, and thereby, the error magnetic fields to be generated at the coil ends 29 and 30 also change. For this reason, the magnetic field correction appropriate for the respective layers can be achieved by changing: the arrangement form of the turns 25 and 26 of the magnetic field correction regions 51C and 52C in the respective layers; the positions of the transition regions 51B and 52B; and the lengths of the transition regions 51B and 52B. Thus, the superconducting coils 23 and 24 with smaller error magnetic fields can be obtained by shortening the coil ends 29 and 30. Note that the magnetic field correction appropriate for the respective layers can be achieved also by changing the positions and lengths of the magnetic field correction regions 51C and 52C.

Figure 13:
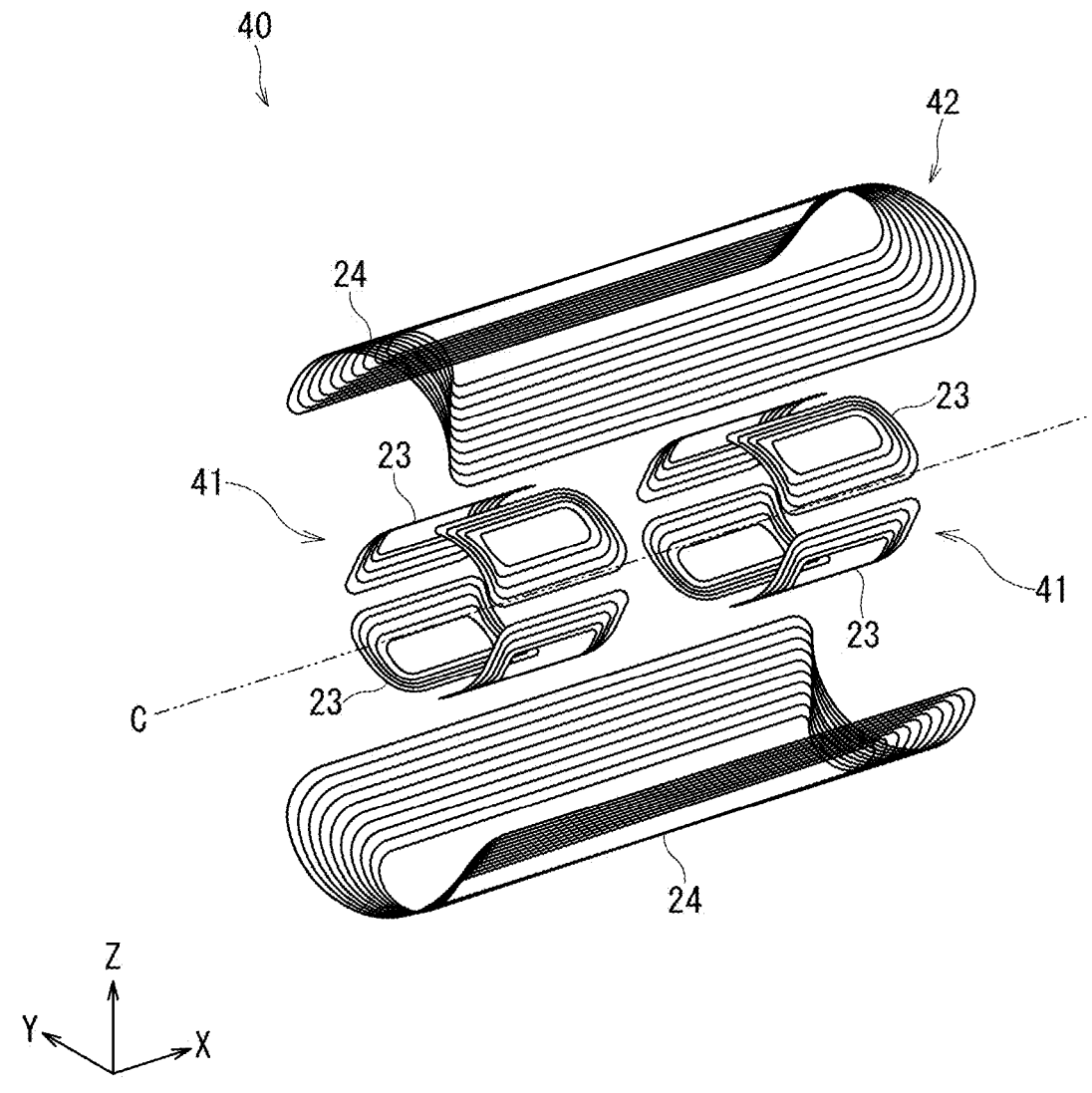
FIG. 13 is an exploded perspective view of a superconducting coil according to a modification.

Next, a description will be given of a superconducting coil apparatus 40 of a modification by referring to FIG. 13. In an exploded perspective view of FIG. 13, in order to facilitate understanding, illustration of the tubular structure is omitted, and only the arrangement aspect of the superconducting coils 23 and 24 is illustrated.

The superconducting coil apparatus 40 of the modification includes: two superconducting quadrupole coils 41 provided in the first layer for generating a quadrupole magnetic field; and one superconducting dipole coil 42 provided in the second layer for generating a dipole magnetic field.

Each superconducting quadrupole coil 41 is formed by four superconducting coils 23. The two superconducting quadrupole coils 41 are arranged side by side in the axial direction (i.e., the X-axis direction).

The one superconducting dipole coil 42 is formed by two superconducting coils 24. The superconducting dipole coil 42 and the superconducting quadrupole coils 41 are arranged coaxially with each other.

The superconducting coil apparatus 40 of the modification can appropriately control the particle beam B with: a dipole magnetic field to be generated by the superconducting dipole coil 42; and a quadrupole magnetic field to be generated by the superconducting quadrupole coils 41.

Although the tubular structures 21 and 22 have an elliptic shape in cross-section in the above-described embodiments, other aspects may be adopted. For example, the tubular structures 21 and 22 may have a perfect circular shape or an oval shape as viewed in cross-section.

Although the tubular structures 21 and 22 have an elliptic shape in which the diameter increases in the bending direction in the above-described embodiments, other aspects may be adopted. For example, the tubular structures 21 and 22 may have an elliptic shape in which the diameter decreases in the bending direction.

Although the boundary line L1 of the superconducting coil 23 of the first layer and the boundary line L2 of the superconducting coil 24 of the second layer are inclined with respect to the reference line K in the same direction in the above-described embodiments, other aspects may be adopted. For example, the boundary line L1 of the superconducting coil 24 of the first layer and the boundary line L2 of the superconducting coil 24 of the second layer may be inclined with respect to the reference line K in directions opposite to each other. In this manner, the magnetic field to be generated at each end of the superconducting coil 23 of the first layer and the magnetic field to be generated at each end of the superconducting coil 24 of the second layer have different forms.

According to the above-described embodiments, the arrangement form of the coil longitudinal portions is different between the main magnetic field generation region configured to generate the main magnetic field and the magnetic field correction region configured to generate the correction magnetic field, which enables reduction in size of the superconducting coil apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A superconducting coil apparatus comprising at least one superconducting coil formed of a plurality of turns under a definition that one turn is a portion of a superconducting wire annularly wound for one round, wherein:

the superconducting coil has a shape along an outer peripheral surface of a tubular structure having a tubular shape;

each of the plurality of turns has a coil longitudinal portion extending along an axial direction of the tubular structure;

arrangement form of the coil longitudinal portion is different between a main magnetic field generation region configured to generate a main magnetic field and a magnetic field correction region configured to generate a correction magnetic field.

2. The superconducting coil apparatus according to claim 1, wherein, in a side view of the tubular structure, a part of the coil longitudinal portion in the magnetic field correction region is displaced in a circumferential direction of the tubular structure.

3. The superconducting coil apparatus according to claim 1, wherein a part of the coil longitudinal portion in the magnetic field correction region is displaced toward an inner peripheral side of the superconducting coil.

4. The superconducting coil apparatus according to claim 1, wherein an end of the coil longitudinal portion is arranged the magnetic field correction region.

5. The superconducting coil apparatus according to claim 4, wherein:

each of the plurality of turns has a coil end extending along a circumferential direction of the tubular structure from the coil longitudinal portion; and the magnetic field correction region is configured to generate a magnetic field that cancels at least an unnecessary magnetic field component to be generated at the coil end.

6. The superconducting coil apparatus according to claim 1, wherein:

a transition region is provided between the main magnetic field generation region and the magnetic field correction region; and a part of the coil longitudinal portion in the transition region is inclined with respect to a part of the coil longitudinal portion in the main magnetic field generation region and the magnetic field correction region.

7. The superconducting coil apparatus according to claim 6, wherein:

the at least one superconducting coil comprises at least two the superconducting coils, the at least two superconducting coils are laminated in a radial direction of the tubular structure; and dimension of the transition region of the superconducting coil of the first layer is different from dimension of the transition region of the superconducting coil of the second layer.

8. The superconducting coil apparatus according to claim 1, wherein the tubular structure is curved with a constant curvature and has an elliptic shape in cross section.

9. The superconducting coil apparatus according to claim 1, wherein the at least one superconducting coil comprises a plurality of the superconducting coils, the superconducting coil apparatus further comprising:

a superconducting dipole coil that is famed of the plurality of superconducting coils and generates a dipole magnetic field; and a superconducting quadrupole coil that is formed of the plurality of superconducting coils and generates a quadrupole magnetic field, wherein the superconducting dipole coil and the superconducting quadrupole coil are arranged coaxially with each other.

10. A superconducting accelerator comprising a plurality of superconducting coil apparatuses, each of which is the superconducting coil apparatus according to claim 1, wherein a beam trajectory for accelerating a particle beam is formed by the plurality of superconducting coil apparatuses.

11. A particle beam therapy apparatus comprising the superconducting accelerator according to claim 10, wherein the superconducting accelerator is configured to accelerate the particle beam in such a manner that a lesion site is irradiated with the particle beam for treatment.

* * * * *